(12) United States Patent
Shakespeare et al.

(10) Patent No.: US 7,859,668 B2
(45) Date of Patent: Dec. 28, 2010

(54) APPARATUS AND METHOD FOR ILLUMINATOR-INDEPENDENT COLOR MEASUREMENTS

(75) Inventors: John F. Shakespeare, Kuopio (FI); Tarja T. Shakespeare, Kuopio (FI)

(73) Assignee: Honeywell International Inc., Morristown, NJ (US)

( * ) Notice: Subject to any disclaimer, the term of this patent is extended or adjusted under 35 U.S.C. 154(b) by 1167 days.

(21) Appl. No.: 11/300,899

(22) Filed: Dec. 15, 2005

(65) Prior Publication Data

US 2007/0139735 A1    Jun. 21, 2007

(51) Int. Cl.
*G01N 21/25*    (2006.01)
(52) U.S. Cl. ........................ 356/407; 356/319
(58) Field of Classification Search ......... 356/319–320, 356/402, 405–407, 414–420, 432–433
See application file for complete search history.

(56) References Cited

U.S. PATENT DOCUMENTS

| | | | |
|---|---|---|---|
| 4,006,358 A | 2/1977 | Howarth |
| 4,288,691 A | 9/1981 | Horton |
| 4,376,946 A | 3/1983 | Kaminow et al. |
| 4,439,038 A | 3/1984 | Mactaggart |
| 4,565,444 A | 1/1986 | Mactaggart |
| 4,592,043 A | 5/1986 | Williams |
| 4,634,928 A | 1/1987 | Figueroa et al. |
| 4,699,510 A | 10/1987 | Alguard |
| 4,786,817 A | 11/1988 | Boissevain et al. |
| 4,807,630 A | 2/1989 | Malinouskas |

(Continued)

FOREIGN PATENT DOCUMENTS

DE    3148076 A1    6/1983

(Continued)

OTHER PUBLICATIONS

Stokman et al., Color Measurement by Imaging Spectrometry, Computer Vision & Image Understanding, San Diego, CA, US, vol. 79, No. 2, Aug. 2000, pp. 236-249.

(Continued)

*Primary Examiner*—Tarifur Chowdhury
*Assistant Examiner*—Tara S Pajoohi
(74) *Attorney, Agent, or Firm*—Munck Carter, LLP

(57) ABSTRACT

A method includes generating at least one first light beam and generating at least one second light beam and at least one third light beam using the at least one first light beam. The at least one first light beam has a plurality of first regions, the at least one second light beam has a plurality of second regions, and the at least one third light beam has a plurality of third regions. Each of the first, second, and third light beams has at least two regions that are spectrally different. The method also includes measuring a spectrum in each of a plurality of first wavelength bands for each of the second regions. The method further includes illuminating at least part of an object with the at least one third light beam to produce at least one fourth light beam. The at least one fourth light beam has a plurality of fourth regions, where at least two of the fourth regions are spectrally different. In addition, the method includes measuring a spectrum in each of a plurality of second wavelength bands for each of the fourth regions and identifying a radiance transfer factor of the object using at least some of the measured spectra.

20 Claims, 6 Drawing Sheets

U.S. PATENT DOCUMENTS

| | | | |
|---|---|---|---|
| 4,856,014 A | 8/1989 | Figueroa et al. |
| 4,883,963 A | 11/1989 | Kemeny et al. |
| 4,928,013 A | 5/1990 | Howarth et al. |
| 5,015,099 A | 5/1991 | Nagai et al. |
| 5,047,652 A | 9/1991 | Lisnyansky et al. |
| 5,122,974 A | 6/1992 | Chance |
| 5,137,364 A | 8/1992 | McCarthy |
| 5,235,192 A | 8/1993 | Chase et al. |
| 5,313,187 A | 5/1994 | Choi et al. |
| 5,338,361 A | 8/1994 | Anderson et al. |
| 5,400,258 A | 3/1995 | He |
| 5,642,189 A | 6/1997 | Alguard |
| 5,642,192 A | 6/1997 | Gordon et al. |
| 5,774,213 A | 6/1998 | Trebino et al. |
| 5,793,486 A | 8/1998 | Gordon et al. |
| 5,795,394 A | 8/1998 | Belotserkovsky et al. |
| 5,821,536 A | 10/1998 | Pettit |
| 5,933,243 A | 8/1999 | Hagen |
| 5,963,333 A | 10/1999 | Walowit et al. |
| 5,992,318 A | 11/1999 | DiBello et al. |
| 6,058,201 A | 5/2000 | Sikes et al. |
| 6,070,093 A * | 5/2000 | Oosta et al. ................. 600/316 |
| 6,074,483 A | 6/2000 | Belotserkovsky et al. |
| 6,263,291 B1 | 7/2001 | Shakespeare et al. |
| 6,272,440 B1 | 8/2001 | Shakespeare et al. |
| 6,466,839 B1 | 10/2002 | Heaven et al. |
| 6,499,402 B1 | 12/2002 | Sikes et al. |
| 6,556,305 B1 | 4/2003 | Aziz et al. |
| 6,584,435 B2 | 6/2003 | Mestha et al. |
| 6,603,551 B2 | 8/2003 | Mestha et al. |
| 6,724,473 B2 | 4/2004 | Leong et al. |
| 6,743,337 B1 | 6/2004 | Ischdonat |
| 6,760,103 B2 | 7/2004 | Shakespeare et al. |
| 6,763,322 B2 | 7/2004 | Potyrailo et al. |
| 6,805,899 B2 | 10/2004 | MacHattie et al. |
| 6,856,436 B2 | 2/2005 | Brukilacchio et al. |
| 6,949,734 B2 | 9/2005 | Neff et al. |
| 7,291,856 B2 | 11/2007 | Haran et al. |
| 2003/0058441 A1 | 3/2003 | Shakespeare et al. |
| 2004/0119781 A1 | 6/2004 | Szumla |
| 2004/0212804 A1 | 10/2004 | Neff et al. |
| 2004/0260520 A1 | 12/2004 | Braendle et al. |
| 2005/0065400 A1 | 3/2005 | Banik et al. |
| 2005/0185179 A1 * | 8/2005 | Wang ........................ 356/328 |
| 2006/0243931 A1 | 11/2006 | Haran et al. |
| 2007/0144388 A1 | 6/2007 | Shakespeare et al. |
| 2007/0153277 A1 | 7/2007 | Shakespeare et al. |
| 2007/0153278 A1 | 7/2007 | Shakespeare et al. |

FOREIGN PATENT DOCUMENTS

| | | |
|---|---|---|
| DE | 19515499 A1 | 10/1996 |
| EP | 0 319 158 A1 | 6/1989 |
| EP | 1437222 A1 | 7/2004 |
| EP | 1457335 A1 | 9/2004 |
| EP | 1 491 877 A1 | 12/2004 |
| WO | WO 03/037111 A1 | 5/2003 |

OTHER PUBLICATIONS

Wandell, Color Measurement and Discrimination, Journal of the Optical Society of America, USA, vol. 2, No. 1, Jan. 1985, pp. 62-71.

Tarja Shakespeare et al., "Problems in Colour Measurement of Fluorescent Paper Grades", Analytica Chimica Acta 380 (1999), pp. 227-242.

Tarja Shakespeare et al., "Advanced Colour Control Through Reflectance Optimization", Proceedings 2nd EcoPaperTech Conference, Helsinki Finland, Jun. 1998, pp. 183-194.

* cited by examiner

APPARATUS AND METHOD FOR ILLUMINATOR-INDEPENDENT COLOR MEASUREMENTS

TECHNICAL FIELD

This disclosure relates generally to color measurement systems and more specifically to an apparatus and method for illuminator-independent color measurements.

BACKGROUND

Different techniques have been developed to identify or measure the color of different objects, such as paper, paint, or plastic. These color measurement techniques typically attempt to provide objective color measurements rather than subjective color measurements. However, conventional color measurement techniques are often poorly suited for measuring or identifying the color of a fluorescent material. A fluorescent material typically represents a material having a luminescence caused by absorption of radiation at one wavelength followed by re-radiation (often at a different wavelength) that ceases when the radiation stops. Conventional color measurement techniques are also often poorly suited for measuring or identifying the color of a phosphorescent material. Phosphorescence is a form of fluorescence where the re-radiation of light energy absorbed at one instant occurs over an extended time rather than at essentially the same instant.

Conventional color measurement techniques typically have difficulty measuring the color of a fluorescent or phosphorescent material for several reasons. One reason is that conventional color measurement techniques are usually based on or descended from techniques for measuring the color of non-fluorescent materials. Non-fluorescent materials usually have a radiance factor that is independent of illumination. In contrast, the radiance factor of a fluorescent or phosphorescent material is often strongly dependent on the spectral power distribution of illumination. In other words, the radiance factor of a fluorescent or phosphorescent material typically varies depending on the light shining on the fluorescent or phosphorescent material during the color measurement.

Conventional color measurement techniques often can accurately characterize the color of a fluorescent or phosphorescent material only for one or several specific illumination conditions. From these measurements, it is usually not possible to accurately predict the color of the fluorescent or phosphorescent material under illumination that differs significantly from the illumination used during the color measurement. This often leads to several problems. For example, there may be large disagreements between manufacturers and customers as to whether a particular object (such as a custom product) satisfies a color specification for that object. Also, this may lead to severe metamerism, where fluorescent or phosphorescent materials that appear substantially identical in color to one color measurement instrument appear substantially different in color to another color measurement instrument. In addition, color measurements made using the conventional color measurement techniques often provide inadequate or misleading information for modeling a coloring process. This often makes it difficult to implement quality control mechanisms for the coloring process and leads to poor quality control performance.

One prior color measurement technique for measuring the color of a fluorescent material involves producing a beam of light having a spectral distribution that varies over time. The beam of light is used to illuminate a material, and spectral power measurements are taken at different times. However, this color measurement technique may require a significant amount of time to work properly. Moreover, when measuring the property of a material that is moving relative to a color measurement instrument, the measurements are typically reliable only if the property does not vary over the distance moved while the measurements are made. For example, in a paper-making machine, a sheet of paper could move at up to 30 meters per second. During this time, only one or two reliable measurements might be formed, and those measurements may be unreliable if the material's property varies over shorter distances.

One prior technique for measuring the color of a phosphorescent material involves continuously illuminating an area of the material with light that spectrally matches the intended illumination in which the material will be used. In this case, light from the sample may include a phosphorescent component as well as fluorescent and reflected or transmitted components. Alternatively, the illumination of the material may be interrupted while the measurement of light from the material continues, allowing the phosphorescence alone to be measured and its variation with time ascertained.

These techniques suffer from the same failings as the conventional measurements of fluorescence, namely that the measurements are not indicative of the color of a material under illumination conditions different from those used for the measurements. Also, if the material exhibits phosphorescence instead of or in addition to fluorescence, the technique in which the spectral distribution of the illumination varies over time may produce incorrect measurements. This is because phosphorescence resulting from illumination at any instant affects the measured light for a significant time after that instant, while the conventional measurement techniques often presume that the measured light varies only in response to the simultaneous variation in illumination. As a result, the time-varying effects on the measurements caused by phosphorescence are conflated with the illumination-varying effects caused by fluorescence. The two effects typically cannot be distinguished, and neither can be reliably quantified from the measurements.

SUMMARY

This disclosure provides an apparatus and method for illuminator-independent color measurements.

In a first embodiment, a method includes generating at least one first light beam having a plurality of first regions. At least two of the first regions are spectrally different. The method also includes generating at least one second light beam and at least one third light beam using the at least one first light beam. The at least one second light beam has a plurality of second regions, and the at least one third light beam has a plurality of third regions. At least two of the second regions are spectrally different, and at least two of the third regions are spectrally different. The method further includes measuring a spectrum in each of a plurality of first wavelength bands for each of the second regions. Moreover, the method includes illuminating at least part of an object with the at least one third light beam to produce at least one fourth light beam. The at least one fourth light beam has a plurality of fourth regions, where at least two of the fourth regions are spectrally different. In addition, the method includes measuring a spectrum in each of a plurality of second wavelength bands for each of the fourth regions and identifying a radiance transfer factor of the object using at least some of the measured spectra.

In particular embodiments, the method includes identifying a color of the object under a specified illumination condition using the radiance transfer factor.

In other particular embodiments, the method includes calibrating first and second detectors used to measure the spectra. The calibration may include using spectrally localized features in one or more regions in each of the second and fourth light beams to calibrate wavelength scales of the detectors. The calibration may also include using spectral features of one or more regions in each of the second and fourth light beams to establish a correspondence between the second and fourth light beams at the detectors. In addition, the calibration may include using a second object having a known reflectance or transmittance to calibrate photometric scales of the detectors.

In a second embodiment, an apparatus includes a beam generator capable of generating at least one first light beam having a plurality of first regions. At least two of the first regions are spectrally different. The beam generator is also capable of generating at least one second light beam and at least one third light beam using the at least one first light beam. The at least one second light beam has a plurality of second regions, and the at least one third light beam has a plurality of third regions. At least two of the second regions are spectrally different, and at least two of the third regions are spectrally different. The apparatus also includes a first detector capable of measuring a spectrum in each of a plurality of first wavelength bands for each of the second regions. The apparatus further includes a second detector capable of measuring a spectrum in each of a plurality of second wavelength bands for each of a plurality of fourth regions in at least one fourth light beam. At least two of the fourth regions are spectrally different. The at least one fourth light beam is generated by illuminating at least part of an object with the at least one third light beam.

In a third embodiment, an apparatus includes beam generating means capable of generating at least one first light beam and generating at least one second light beam and at least one third light beam using the at least one first light beam. The at least one first light beam has a plurality of first regions, the at least one second light beam has a plurality of second regions, and the at least one third light beam has a plurality of third regions. At least two of the first regions are spectrally different, at least two of the second regions are spectrally different, and at least two of the third regions are spectrally different. The apparatus also includes first measuring means capable of measuring a spectrum in each of a plurality of first wavelength bands for each of the second regions. The apparatus further includes second measuring means capable of measuring a spectrum in each of a plurality of second wavelength bands for each of a plurality of fourth regions in at least one fourth light beam. At least two of the fourth regions are spectrally different. The at least one fourth light beam is generated by illuminating at least part of an object with the at least one third light beam.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
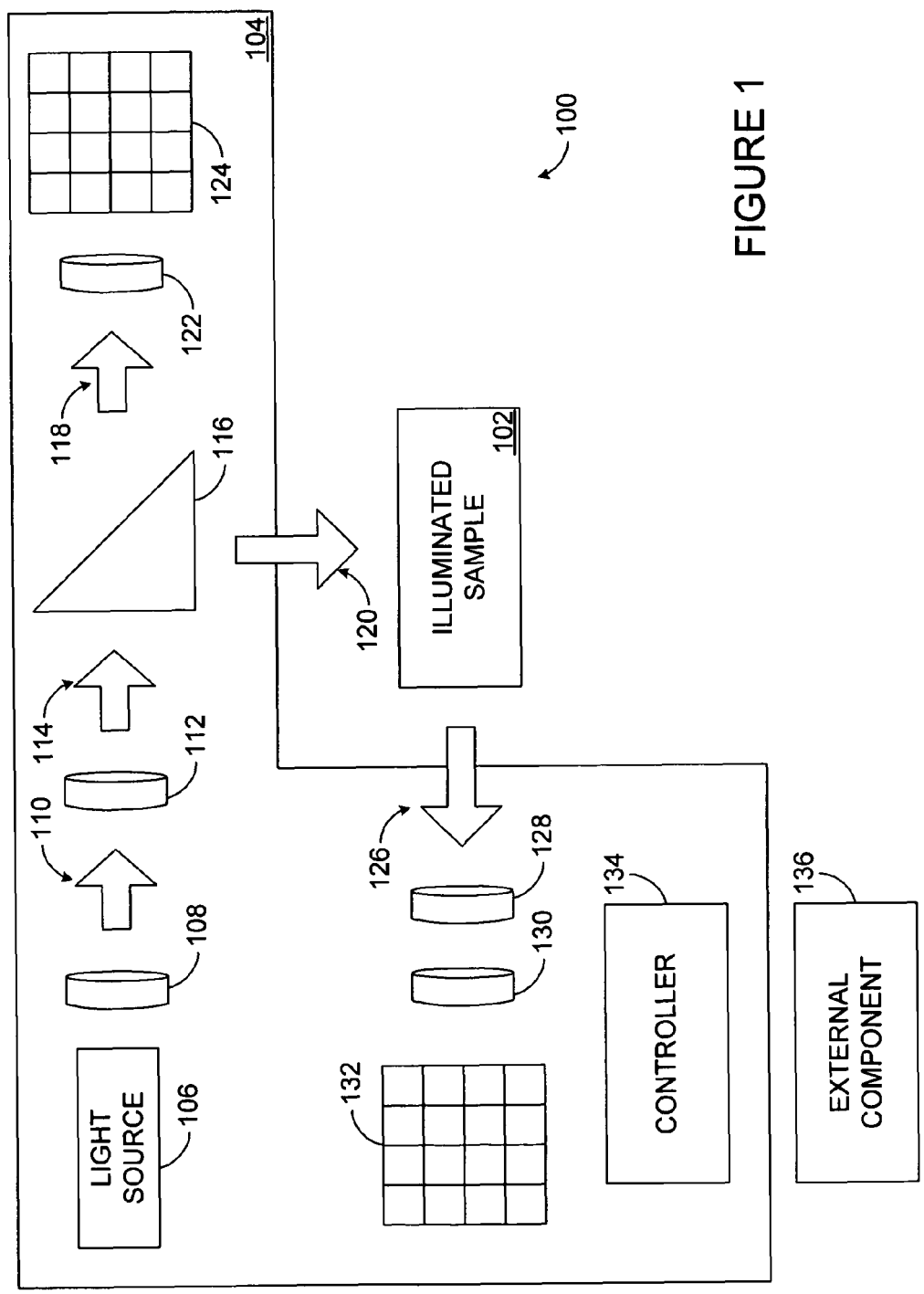
FIG. 1 illustrates an example system for illuminator-independent color measurements according to one embodiment of this disclosure.

FIG. 1 illustrates an example system 100 for illuminator-independent color measurements according to one embodiment of this disclosure. The embodiment of the system 100 shown in FIG. 1 is for illustration only. Other embodiments of the system 100 may be used without departing from the scope of this disclosure.

In this example, the system 100 includes a sample 102 and a color measurement device 104. In general, the sample 102 represents a product, device, material, substance, or other object to be analyzed by the color measurement device 104. The sample 102 could, for example, represent a paper, paint, or plastic product. As a particular example, the sample 102 could represent a paper product having an optical brightener, such as stilbene compounds having an excitation range of 330-420 nm and an emission range from 380-500 nm. As another particular example, the sample 102 could represent a paper product or other product having a fluorescent or phosphorescent color. Any other suitable sample 102 could be used in the system 100, whether the sample 102 includes an optical brightener or has a fluorescent or phosphorescent color.

The color measurement device 104 analyzes the sample 102 and generates information associated with the color of the sample 102. For example, the color measurement device 104 could measure the radiance factor of the sample 102 under multiple illumination conditions at the same time. The color measurement device 104 could also measure the spectral power distributions of the different illumination conditions. The color measurement device 104 may perform these functions without requiring the use of any specific illumination condition. Using these measurements, a characterization of color that is independent of the illumination can be identified, such as by determining the radiance transfer factor of the sample 102. Using the radiance transfer factor, the color of the sample 102 under an arbitrary illumination condition can be predicted. This may allow, for example, a manufacturer or other entity to predict the color of the sample 102 under various illumination conditions.

In this example embodiment, the color measurement device 104 includes a light source 106. The light source 106 provides illumination used to analyze the sample 102. For example, the light source 106 could provide rich spectrum light. As a particular example, the light source 106 could provide adequate light emission at most or all wavelengths throughout a wavelength range of interest. In particular embodiments, bands of inadequate spectral power within a wavelength range may be acceptable if the bands are narrower than the bandpass of various detectors in the color measurement device 104. The light source 106 represents any suitable source of light, such as a rich-spectrum light source or a narrow-band light source.

Light from the light source 106 passes through a diffuser-collimator 108. The diffuser-collimator 108 diffuses light from the light source and collimates the light. This produces a broad collimated, spectrally uniform light beam 110. The diffuser-collimator 108 represents any suitable structure or structures for diffusing and collimating light.

The light beam 110 passes through a filter 112. The filter 112 filters the light beam 110 to produce a broad collimated, spectrally variable light beam 114. The light beam 114 contains multiple spatial regions, where each region is spectrally homogenous and at least two of the spatial regions are spectrally different. The filter 112 includes any suitable structure or structures for producing spectrally variable light. The filter 112 could, for example, represent a filter that is spatially variable along a one-dimensional axis. Also, the filter 112 may provide a range of different rich spectra as an output and need not provide only a monochrome spectra or a narrow band of spectra as an output. In this document, the phrase "spectrally homogenous" need not require that a spectrum be of equal amplitude at all wavelengths and may include a spectrum that is the same or substantially the same at any point in some particular spatial region.

A splitter 116 splits the light beam 114 into a reference beam 118 and a probe beam 120. The splitter 116 represents any suitable structure or structures for splitting a beam of light into multiple beams. The splitter 116 could, for example, represent an achroic beam splitter. The splitter 116 could split the light beam 114 so as to preserve the spectrally different regions of the beam 114 in the reference beam 118 and the probe beam 120. The division ratio of the splitter 116 need not be the same for all regions. The relative spectral power distribution may be the same or relatively the same in corresponding regions of the beams 118-120.

The reference beam 118 is provided to a dispersive element 122. The dispersive element 122 disperses the reference beam 118 by spreading the reference beam 118 along a second one-dimensional axis. For example, the reference beam 118 could include multiple spectrally homogenous spatial regions, and the dispersive element 122 could disperse each of these spectrally homogenous regions into multiple wavelength bands. The dispersive element 122 includes any suitable structure or structures for dispersing light.

The dispersed light from the dispersive element 122 is received at a reference detector array 124. The reference detector array 124 is capable of measuring the amount of light in various portions of the dispersed reference beam. For example, each row of the reference detector array 124 could measure the spectra in the wavelength bands for a single spectrally homogenous region in the reference beam 118. Also, each column of the reference detector array 124 could be associated with different spectrally homogenous regions in the reference beam 118. The reference detector array 124 includes any suitable structure or structures for measuring light.

As shown in FIG. 1, the probe beam 120 illuminates at least part of the sample 102. The probe beam 120 interacts with the sample 102 to produce a measurement beam 126. The measurement beam 126 may be produced by being remitted from or by being transmitted through the sample 102 and may include fluorescent or phosphorescent emission stimulated by the probe beam 120. The measurement beam 126 may have multiple regions with different spectral power distributions. The different spectral power distributions may be caused, among other things, by the interaction of the sample 102 with the probe beam 120.

The measurement beam 126 passes through a lens 128 and a dispersive element 130. The lens 128 focuses the measurement beam 126, and the dispersive element 130 disperses the focused measurement beam 126 along the second one-dimensional axis. The lens 128 includes any suitable structure or structures for focusing light, and the dispersive element 130 includes any suitable structure or structures for dispersing light. As a particular example, the dispersive element 130 could disperse each spectrally homogenous region of the measurement beam 126 into multiple wavelength bands.

The dispersed light from the dispersive element 130 is received at a measurement detector array 132. The measurement detector array 132 measures the amount of light in various wavelength bands associated with each spectrally homogenous region of the measurement beam 126. The measurement detector array 132 may operate in a similar manner as the reference detector array 124. The measurement detector array 132 includes any suitable structure or structures for measuring light.

In some embodiments, the lens 128, dispersive element 130, and measurement detector array 132 are located on the same side of the sample 102 as the other components of the color measurement device 104. In these embodiments, the lens 128, dispersive element 130, and measurement detector array 132 are said to reside on the same side of the sample 102 as the incidence of the probe beam 120. This configuration may be useful, for example, when the measurement beam 126 is reflected from the sample 102. In other embodiments, the lens 128, dispersive element 130, and measurement detector array 132 are located on the opposite side of the sample 102 as the other components of the color measurement device 104. In these embodiments, the lens 128, dispersive element 130, and measurement detector array 132 are said to reside on the opposite side of the sample 102 as the incidence of the probe beam 120. This configuration may be useful, for example, when the measurement beam 126 is formed when the probe beam 120 is transmitted through the sample 102. Any other or additional configurations could also be used.

In some embodiments, the detector arrays 124 and 132 could represent arrays of detectors, such as Charge-Coupled Device (CCD) or Complementary Metal-Oxide Semiconductor (CMOS) image detectors. In other embodiments, either or both of the detector arrays 124 and 132 could be replaced by multiple array detectors or by a set of suitably located linear detectors. This may be useful, for example, when the respective light beams to be measured cannot be brought to a sufficiently compact area for use of a single detector array.

The measurements made by the detector arrays 124 and 132 may be used to determine the radiance transfer factor of the sample 102. The radiance transfer factor of the sample 102 may then be used to predict the color and/or related properties of the sample 102 under an arbitrary light source. In some embodiments, these calculations are performed by a controller 134 in the color measurement device 104. In these embodiments, the controller 134 represents any hardware, software, firmware, or combination thereof for determining the radiance transfer factor and/or predicting the color of the sample 102. In other embodiments, the controller 134 could collect the outputs from the detector arrays 124 and 132 and provide the data to an external component 136 (such as an external controller or computing device), where the external component 136 calculates the radiance transfer factor and/or predicts the color of the sample 102. In yet other embodiments, the outputs from the detector arrays 124 and 132 could be provided directly to the external component 136.

In this way, the radiance transfer factor of the sample 102 may be determined and used to predict the color of the sample 102 under a specified lighting condition. Also, by making measurements with multiple illumination spectra simultaneously, it may be possible to determine the radiance transfer factor of the sample 102 more quickly and reliably. This may remain true even if the sample 102 is moving or the radiance transfer factor is varying quickly over time. Further, the illuminated area of the sample 102 need not be large for the probe 120 beam, so the measured area of the sample 102 can be quite compact. This may make it possible to measure variations in the radiance transfer factor of a moving sample 102 over relatively short distances. In addition, it may be possible to measure many different samples 102 in a short period of time.

In addition, by illuminating a sample 102 with non-time varying illumination and then interrupting the illumination and continuing to take measurements of the measurement beam 126, the phosphorescence of the sample 102 can be quantified. For example, the phosphorescence may be quantified as a time-dependent radiance transfer factor for a time lag from the time at which the illumination is interrupted to a time at which a measurement is made. This type of time-dependent radiance transfer factor may represent the step response or decay of phosphorescence, and it may be converted into an impulse response or any other convenient time-dependent form. The radiance transfer factor obtained from measurements with continuous illumination can then be decomposed into a fluorescent radiance transfer factor and a phosphorescent radiance transfer factor.

Figure 2:
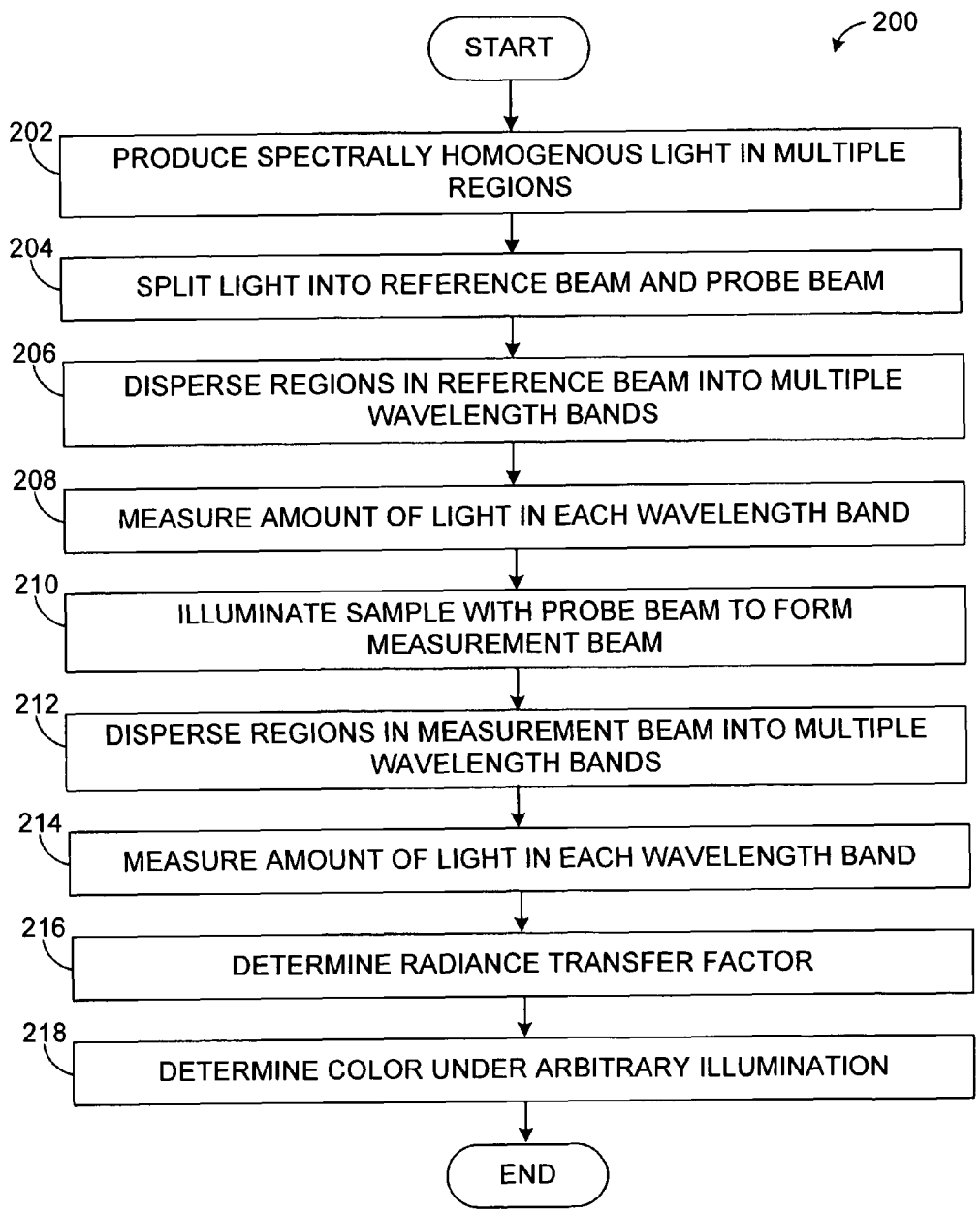
FIG. 2 illustrates an example method for illuminator-independent color measurements according to one embodiment of this disclosure.
Figure 3:
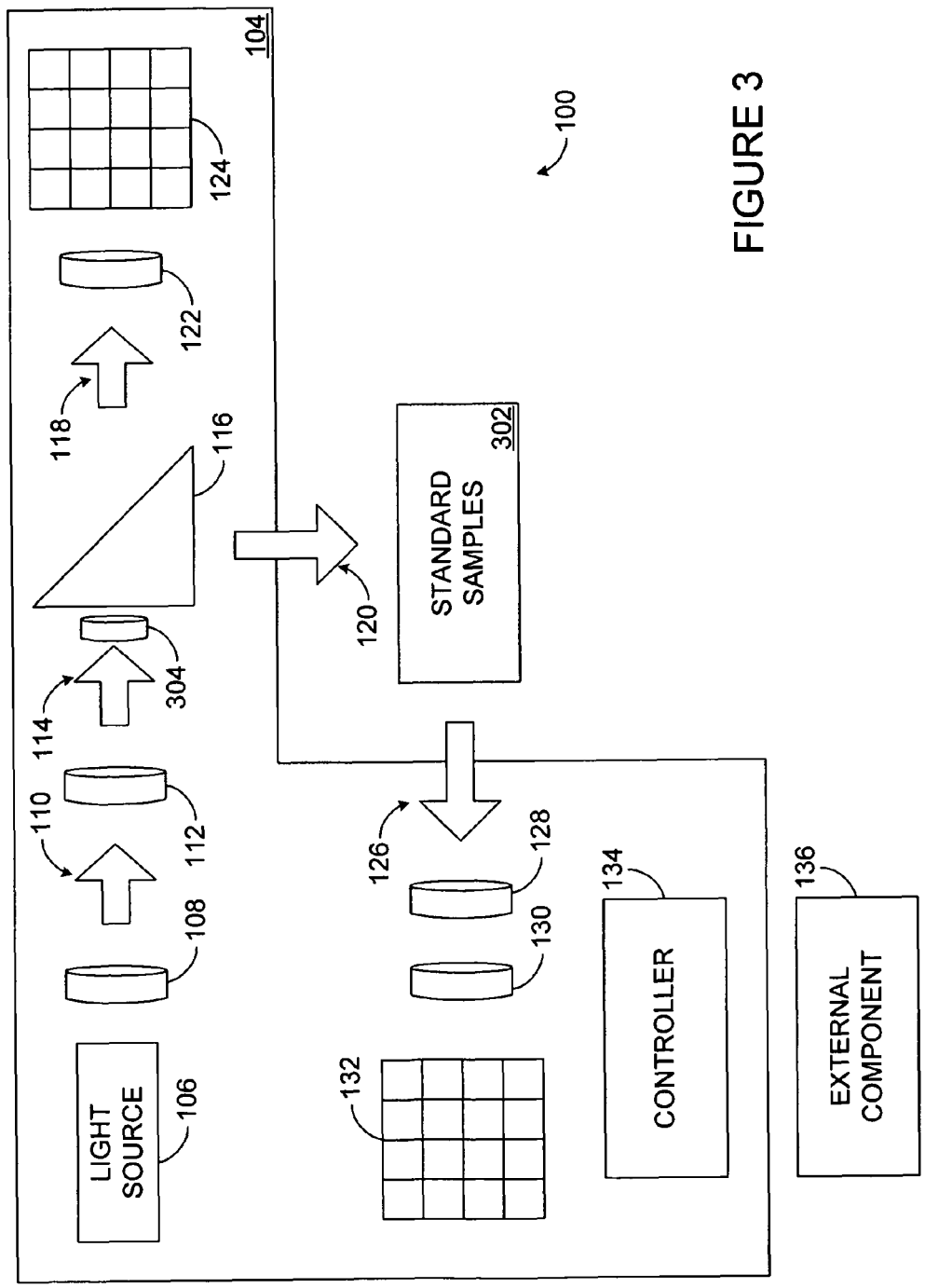
FIG. 3 illustrates additional details of the system of FIG. 1 during calibration according to one embodiment of this disclosure.
Figure 4:
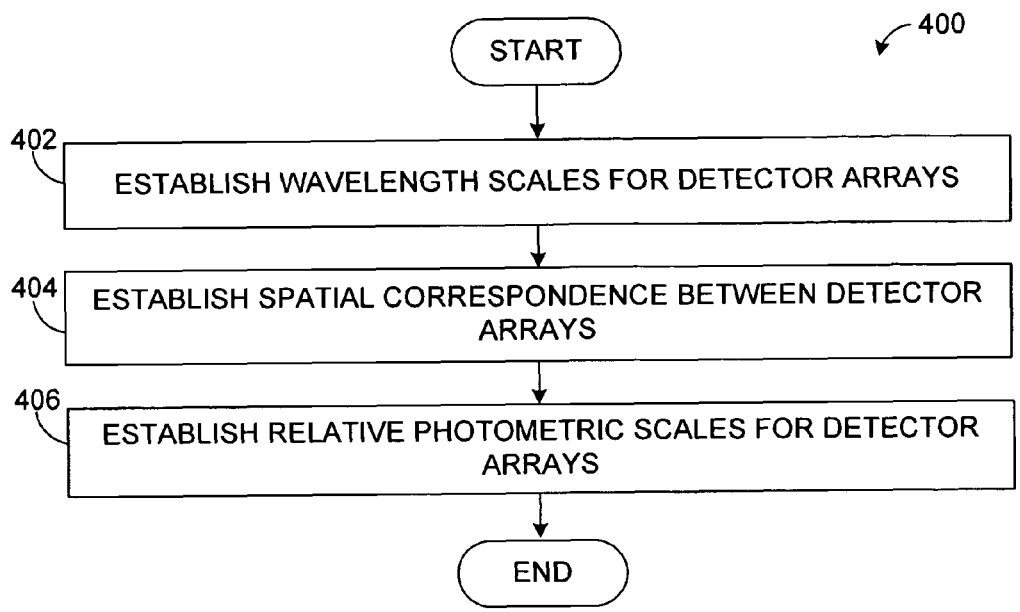
FIG. 4 illustrates an example method for calibrating a system for illuminator-independent color measurements according to one embodiment of this disclosure.

Additional details regarding the operation of the color measurement device 104 are provided in FIG. 2. Prior to normal operation, the color measurement device 104 may be calibrated so that proper results can be obtained. Additional details about the calibration of the color measurement device 104 are shown in FIGS. 3 and 4. FIGS. 5A through 5E illustrate possible modifications to the color measurement device 104.

Although FIG. 1 illustrates one example of a system 100 for illuminator-independent color measurements, various changes may be made to FIG. 1. For example, while described as using or producing single beams of light (such as beams 110, 114, 118, 120, and 126), each of these beams could represent multiple beams of light. Also, the use of the controller 134 in the color measurement device 104 is optional. Similarly, while reference has been made to a lens 128, light can be focused onto the dispersive element 130 by a mirror or other suitable mechanism. Moreover, in some measurement geometries, the lens 128 can be omitted if the dispersive element 130 can be positioned in suitably close proximity to the illuminated sample 102. Further, certain components shown as distinct entities in FIG. 1 may be combined into integrated components. As a particular example, the beam splitter 116 and the filter 112 could be constructed as a single component, in which case the beam 114 exists within the component rather than in transit between the components. In addition, while reference has been made to collimated beams, in other embodiments a diffusing mechanism for one or more probe beams 120 may be used so that the sample 102 is illuminated by at least one diffuse radiance. In this case, the diffusing mechanism could diffuse one probe beam 120 in close enough proximity to the sample 102 so that the resulting diffuse radiance does not significantly overlap the radiance from any other probe beam 120.

FIG. 2 illustrates an example method 200 for illuminator-independent color measurements according to one embodiment of this disclosure. For ease of explanation, the method 200 is described with respect to the color measuring device 104 operating in the system 100 of FIG. 1. The method 200 could be used in any other suitable device and in any other suitable system.

Light is produced that is substantially or essentially homogenous spectrally in each of multiple spatial regions at step 202. This may include, for example, the light source 106, diffuser-collimator 108, and filter 112 producing one or more spectrally variable light beams 114. At least two spatial regions in the one or more beams 114 contain light that is spectrally different. Let the spectral power distributions in m of these spatial regions be denoted as $E_1(\lambda), E_2(\lambda), \ldots, E_m(\lambda)$.

The light is split into at least one reference beam and at least one probe beam at step 204. This may include, for example, the splitter 116 splitting the one or more spectrally variable light beams 114 into one or more reference beams 118 and one or more probe beams 120. The one or more reference beams 118 may include multiple spatial regions that are substantially or essentially homogenous spectrally. Similarly, the one or more probe beams 120 may include multiple spatial regions that are substantially or essentially homogenous spectrally. The splitting of spatial region k in the light beam 114 may produce a region of the probe beam 120 having a spectral power distribution $\alpha_k E_k(\lambda)$. The splitting of the spatial region k may also produce a region of the reference beam 118 having a spectral power distribution $\beta_k E_k(\lambda)$, where $\alpha_k + \beta_k \leq 1$.

Each spectrally homogenous region of the one or more reference beams 118 are dispersed into multiple wavelength bands at step 206, and the amount of light in each wavelength band is measured at step 208. This may include, for example, passing the one or more reference beams 118 through the dispersive element 122. This forms an array of reference spectra, which is measured by the reference detector array 124. With n wavelength bands and non-ideal dispersion, the reference spectra form an array S. Elements in the array S may be defined as:

$$S_{ki} = \beta_k(\ldots + a_{-1} E_k(\lambda_i) + a_0 E_k(\lambda_i) + a_1 E_k(\lambda_{i+1}) + \ldots), k=1:m, i=1:n \quad (1)$$

where $a_{-1}$, $a_0$, $a_1$, and so forth represent convolution coefficients describing the non-ideality of the dispersive element 122 onto the reference detector array 124. Deconvoluting the array S to cancel the dispersion non-ideality may result in:

$$S_{ki} = \beta_k E_k(\lambda_i), k=1:m, i=1:n. \quad (2)$$

At least part of a sample 102 is illuminated using the one or more probe beams 120 to produce one or more measurement beams 126 at step 210. The one or more measurement beams 126 may include multiple spatial regions that are substantially or essentially homogenous spectrally. Let the radiance transfer factor of the sample 102 be denoted as $B(\xi,\lambda)$ with discrete representation B whose elements $B_{ji}$ are narrow-band integral norms. The radiance transfer factor $B(\xi,\lambda)$ may describe the excident radiant power from an object at wavelength $\lambda$ (or in a narrow band of wavelengths around $\lambda$) produced in response to illumination with incident radiance of unit power at wavelength $\xi$ (or in a narrow band of wavelengths around $\xi$). $B(\xi,\lambda)$ typically does not contain negative values and contains nonzero values for $\lambda \geq \xi$. The diagonal values $B(\lambda,\lambda)$ describe the effects of conventional reflection or transmission, depending on the relative geometry of illumination and detection. The off-diagonal values $B(\xi,\lambda)$ with $\lambda > \xi$ describe the effects of fluorescence (if any is present). The off-diagonal values $B(\xi,\lambda)$ with $\lambda < \xi$ may be zero. The region of the measurement beam 126 corresponding to region k of the probe beam 120 may have a spectral power distribution of:

$$P_k = \alpha_k B E_k, k=1:m. \quad (3)$$

Each spectrally homogenous region of the one or more measurement beams 126 is dispersed into multiple wavelength bands at step 212, and the amount of light in each wavelength band is measured at step 214. This may include, for example, passing the one or more measurement beams 126 through the lens 128 and the dispersive element 130. This forms an array of measurement spectra, which is measured by the measurement detector array 132. With n wavelength bands and non-ideal dispersion, the measurement spectra form an array P. Elements in the array P may be is defined as:

$$P_{ki}=\alpha_k(\ldots +a_{-1}BE_k(\lambda_{i-1})+a_0BE_k(\lambda_i)+a_1BE_k(\lambda_{i+1})+\ldots), k=1:m, i=1:n. \quad (4)$$

where $a_{-1}$, $a_0$, $a_1$, and so forth represent convolution coefficients describing the non-ideality of the dispersive element 130 onto the measurement detector array 132. Deconvoluting the array P to cancel the dispersion non-ideality may result in:

$$P_{ki}=\alpha_k BE_k(\lambda_i), k=1:m, i=1:n. \quad (5)$$

The radiance transfer factor of the sample 102 is determined using the measurements of the one or more reference beams 118 and the one or more measurement beams 126 at step 216. This may include, for example, the controller 134 or an external component 136 calculating the radiance transfer factor. As a particular example, let each of the measurement spectra P and the reference spectra S be divided by an appropriate scalar factor $\alpha_k$ or $\beta_k$. A least-squares estimate of B may be obtained as:

$$B=PS^T(SS^T)^{-1} \quad (6)$$

where $S^T$ represents a transpose of array S. A constrained least-squares estimate could also be used here, since B may be either triangular or diagonal and may not contain any negative values. This calculation may be useful, for example, in fluorescent wavelength ranges, and $SS^T$ may need a complete rank only in those sub-blocks. At wavelengths where a sample 102 is known not to exhibit fluorescence, B could represent a diagonal matrix, and element by element division of $B_{ii}=P_{ki}/S_{ki}$ (mean or weighted mean of k=1:m) could replace this matrix operation.

A calculation or estimation of a phosphorescent radiance transfer factor may proceed in a similar manner. The illumination of the sample 102 is interrupted, and the last measurement time before the interruption is designated $t_0$. The reference illumination $E_k$ for each spectrally homogenous region at time to or averaged over a period ending not later than time to may be used in estimating the phosphorescent radiance transfer factor. For example, a time-dependent radiance transfer factor B(t) may be calculated from the measurements $S_k(t)$ at each subsequent instant t. As a particular example, a least-squares estimate can be obtained for B(t) using the equation:

$$B(t)=P(t)E^T(t_0)(E(t_0)E(t_0)^T)^{-1}. \quad (7)$$

In this example, the phosphorescent radiance transfer factor in matrix form may be triangular and may contain exclusively off-diagonal non-negative values. A constrained least-squares or other estimation method could incorporate these known conditions.

The color and/or other related properties of the sample 102 for an arbitrary illumination are determined at step 218. This may include, for example, the controller 134 or an external component 136 identifying the color of the sample 102 using the measurements obtained during steps 208 and 214. As a particular example, let $T(\lambda)$ represent a designated light source. The color of the sample 102 under this light source could be determined using a simulated measurement BT. The simulated measurement BT can be used to compute color coordinates, such as International Commission of Illumination (CIE) L*a*b parameters or International Organization for Standardization (ISO) brightness parameters. These color coordinates could be determined as if the simulated measurement BT had occurred using an actual light source. Similarly, by computing simulated measurements for two designated light sources $T_1$ and $T_2$, it may be possible to accurately compute an index of illuminator metamerism for that source pair. Illuminator metamerism may differ from illuminant metamerism when fluorescence or phosphorescence is present, and illuminator metamerism may be accurately determined when measurements are available using the designated pair of light sources.

Although FIG. 2 illustrates one example of a method 200 for illuminator-independent color measurements, various changes may be made to FIG. 2. For example, while shown as a series of steps in FIG. 2, various ones of the steps in FIG. 2 may occur in parallel. This may occur, for example, when steps 206-208 dealing with the reference beam(s) 118 occur in parallel with steps 210-214 involving the probe beam(s) 120.

FIG. 3 illustrates additional details of the system 100 of FIG. 1 during calibration according to one embodiment of this disclosure. The mechanism for calibrating the system 100 shown in FIG. 3 is for illustration only. Other techniques for calibrating the system 100 could be used without departing from the scope of this disclosure.

As shown in FIG. 3, the sample 102 from FIG. 1 has been replaced by one or more standard samples 302. Also, a wavelength calibration filter 304 has been inserted between the filter 112 and the splitter 116. The standard samples 302 may be used for photometric calibration of the measurement detector array 132 and for relative calibration of the reference detector array 124. For example, the standard samples 302 may provide one or more grey-level standards having a reflectance or transmittance that is known with respect to a perfect diffuser. Instead of or in addition to this, the standard samples 302 could provide one or more chromatic, fluorescent, or phosphorescent standards having known characteristics.

The wavelength calibration filter 304 is used to support relative alignment of the detector arrays 124 and 132. For example, the wavelength calibration filter 304 could produce a light beam having well-localized spectral features in a limited or reduced number of areas of the light beam. Using the light beam produced by the wavelength calibration filter 304, the detector arrays 124 and 132 can be suitably positioned in the color measurement device 104. The wavelength calibration filter 304 could represent any suitable structure or structures for creating transitions at known wavelengths, such as one or more holmium (Ho), praseodymium (Pr), or neodymium (Nd) glass filters or suitably chosen interference filters.

Although FIG. 3 illustrates one example of a calibration mechanism for calibrating the system 100 of FIG. 1, various changes may be made to FIG. 3. For example, the multiple standard samples 302 could be replaced by a single sample having different regions with different known reflectances or transmittances. Also, multiple wavelength calibration filters 304 could be used to calibrate the system 100.

FIG. 4 illustrates an example method 400 for calibrating a system for illuminator-independent color measurements according to one embodiment of this disclosure. For ease of explanation, the method 400 is described with respect to the color measuring device 104 operating in the system 100 of FIG. 1. The method 400 could be used in any other suitable device and in any other suitable system.

Wavelength scales for the detector arrays 124 and 132 are established at step 402. This may include, for example, imposing spectrally localized features on at least one light beam. As a particular example, this may include imposing spectrally localized features on one or more spectrally variable light beams 114 using one or more wavelength calibration filters 304. This may impose sharp transitions at multiple known wavelengths of the light beam 114. The wavelength scale for each of the detector arrays 124 and 132 may then be established by identifying the corresponding shifts between neighboring elements of the detector arrays 124 and 132. In particular embodiments, a grey-level standard is used as the sample 302 during this step.

Spatial correspondence between the detector arrays 124 and 132 is established at step 404. This may include, for example, imposing characteristic spectral features on at least one spectrally homogenous spatial region of at least one light beam, where the spectral features for that region differ from neighboring regions. As a particular example, this may include imposing the characteristic spectral features on at least one region of the light beam 114 using the one or more wavelength calibration filters 304. The region on which the characteristic spectral features are imposed may be clearly distinguishable spectrally from the neighboring regions. The one or more wavelength calibration filters 304 could be used only during this step and the prior step, or the calibration filters 304 could also be used during normal operation of the color measurement device 104.

Relative photometric scales for the detector arrays 124 and 132 are established at step 406. This may include, for example, using standard samples 302 having known spectral characteristics. In some embodiments, absolute photometric scales need not be determined in this step. As a specific example, for a reflective or transmissive standard sample 302 that is not fluorescent or phosphorescent, the ratio of powers in corresponding elements of the detector arrays 124 and 132 is ideally proportional to the reflectance or transmittance of the sample 302 at a given wavelength. Also, it is possible to use multiple standard samples 302 having different reflectances or transmittances during this step so that deviations from photometric linearity can be determined.

Although FIG. 4 illustrates one example of a method 400 for calibrating a system for illuminator-independent color measurements, various changes may be made to FIG. 4. For example, while the wavelength scale and spatial correspondence steps 402-404 are shown as separate steps in FIG. 4, these steps could be combined into a single step. As a particular example, this may involve imposing spectrally localized features that are not the same for all spatial regions, such as by using alternating holmium and neodymium glass filters.

FIGS. 5A through 5E illustrate example modifications to the system 100 of FIG. 1 according to one embodiment of this disclosure. The modifications shown in FIGS. 5A through 5E are for illustration only. Any of these or other modifications or a combination of these or other modifications could be used in the system 100 of FIG. 1 without departing from the scope of this disclosure.

Figure 5A:
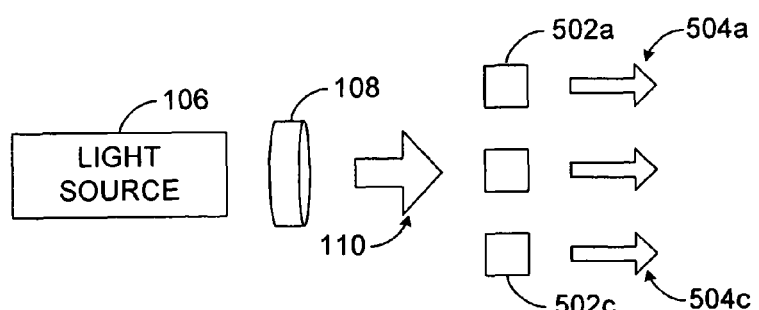
FIGS. 5A through 5E illustrate example modifications to the system of FIG. 1 according to one embodiment of this disclosure.

As shown in FIG. 5A, the filter 112 (having a one-dimensional spatial variation) in FIG. 1 may be replaced by multiple filters 502a-502c. At least some of the filters 502a-502c have different spectral pass characteristics. Also, each of these filters 502a-502c could be uniform, or some or all of the filters 502a-502c could have different regions with different spectral pass characteristics. To support wavelength calibration and relative alignment of the detector arrays 124 and 132, at least one of the filters 502a-502c could have localized spectral features, which may or may not be used only during calibration.

Figure 5B:
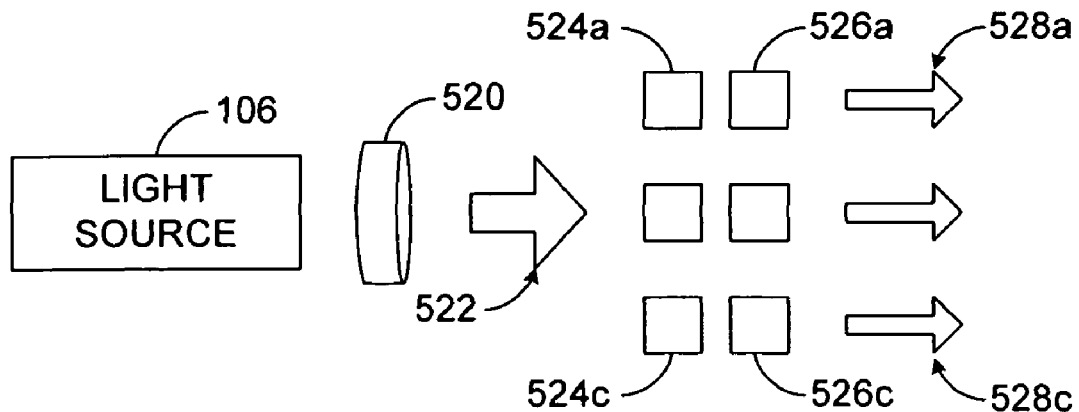

As shown in FIG. 5B, the diffuser-collimator 108 of FIG. 1 may be replaced by at least one diffuser 520, which diffuses light from the light source 106. This produces one or more spectrally uniform light beams 522, which have not been collimated. Also, lenses 524a-524c and filters 526a-526c may be used to produce multiple focused light beams 528a-528c. The focused light beams 528a-528c can be focused on a sample 102 through the splitter 116. Mirrors or refractive elements could also be used to focus the light beams 528a-528c onto the sample 102. In this case, the distance of the sample 102 may be constrained so that the sample 102 remains within range of the working distance of the optics. Also, in this example, the dispersive element 122 and the reference detector array 124 could include suitable focusing optics to process multiple reference beams 118 produced when splitting the light beams 528a-528c.

Figure 5C:
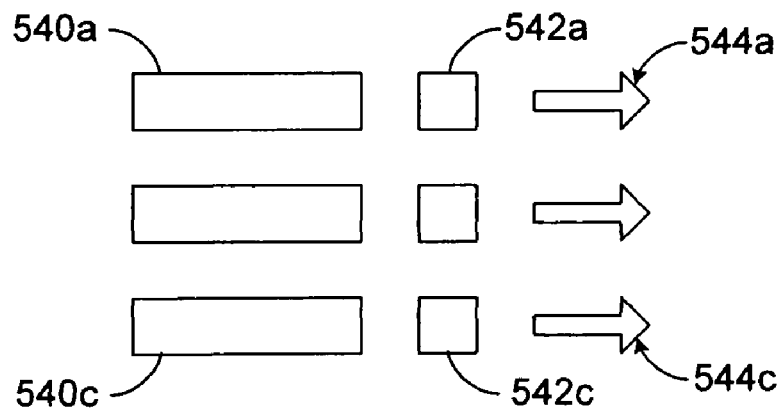

As shown in FIG. 5C, the single light source 106 in FIG. 1 may be replaced by a set of light sources 540a-540c. In some embodiments, each of the light sources 540a-540c may represent a spectrally-incomplete light source having inadequate light emissions at one or more wavelength ranges. These spectrally-incomplete light sources 540a-540c could, for example, represent fluorescent tubes. Light from the light sources 540a-540c passes through multiple lenses or collimators 542a-542c to produce multiple focused or collimated light beams 544a-544c, and filters may or may not be used. The light beams 544a-544c may have variant spectra.

Figure 5D:
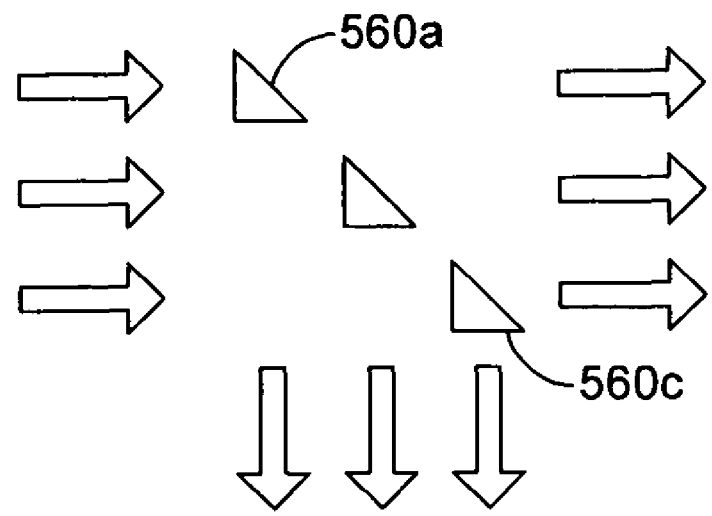

As shown in FIG. 5D, the single splitter 116 in FIG. 1 may be replaced by multiple splitters 560a-560c. This may be useful, for example, if any of the modifications in FIGS. 5A through 5C are used to produce multiple light beams. The splitters 560a-560c can be arranged in a linear pattern, a rectangular pattern, or any other suitable manner. Also, the splitters 560a-560c could be arranged so as to re-order the output light beams, so the arrangement of the light beams illuminating the sample 102 is different from the arrangement of light beams on the reference detector array 124.

Figure 5E:
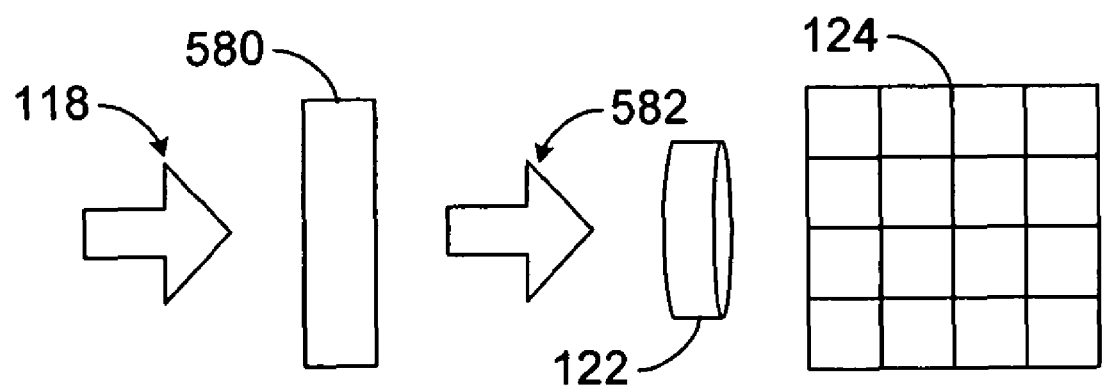

As shown in FIG. 5E, a reference sample 580 may be inserted between the reference beam 118 and the dispersive element 122. The reference sample 580 could represent any suitable sample having any suitable known reflectance or transmittance. A light beam 582 is produced by interaction of the reference beam 118 and the reference sample 580. The light beam 582 is then passed through the dispersive element 122 onto the reference detector array 124. In this example, the geometrical relationship between the reference beam 118, the reference sample 580, and the reference detector array 124 may correspond to the geometrical relationship between the probe beam 120, the sample 102, and the measurement detector array 132.

Although FIGS. 5A through 5E illustrate examples of modifications that could be made to the system 100 of FIG. 1, various changes may be made to FIGS. 5A through 5E. For example, the use of three components (such as three filters, lenses, or splitters) in FIGS. 5A through 5D is for illustration only. Any suitable number of these components could be used in the system 100. Also, FIGS. 5A through 5E are not intended to represent all envisioned modifications to the system 100. Any other or additional modifications could be made to the system 100, and any combination of modifications could be used in the system 100.

It may be advantageous to set forth definitions of certain words and phrases used throughout this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. For example, measurements of a partly opaque material on backings of different reflectivity can be used to infer the material's transmission properties, compute the properties of an essentially opaque stack formed from the material, or distinguish between absorption and scattering effects in the radiance transfer factor. Instead of using a reflective measurement with backings of different properties for this purpose, it may also be possible to measure simultaneously both the reflected and transmitted light from the material. As another example, by making a known perturbation to a process that produces a material, the radiance transfer factor of the material may be measured before and after the perturbation. It may then be possible to characterize the radiance transfer factor response of the process to the perturbation and hence to quantify the color response in the material for any designated illuminator. Moreover, by using color measurements estimated for multiple illuminators and the color responses computed for those illuminators, it may be possible to control illuminator metamerism of a material by manipulating the addition of colorants to the manufacturing process. An apparatus according to this disclosure may be deployed to measure a material in one or more fixed locations or traverse across the material to sequentially measure its properties in multiple locations. The apparatus could also be equipped with light pipes or moveable mirrors that can convey light beams to multiple locations across the material and that can convey reflected or transmitted light from the material at those locations to the detector so that the material can be measured at multiple locations more rapidly. These variants may be particularly useful in making measurements of moving materials during manufacturing or processing of the materials. Accordingly, the above description of example embodiments does not define or constrain this disclosure. Other changes, substitutions, and alterations are also possible without departing from the spirit and scope of this disclosure, as defined by the following claims.

What is claimed is:

1. A method, comprising:
   generating a first light beam comprising a plurality of first spatial regions, at least two of the first spatial regions being spectrally different;
   generating at least one second light beam and at least one third light beam using the first light beam, the at least one second light beam comprising a plurality of second spatial regions, each of the second spatial regions comprising a plurality of first wavelength bands, the at least one third light beam comprising a plurality of third spatial regions, at least two of the second spatial regions being spectrally different, at least two of the third spatial regions being spectrally different;
   measuring a spectrum in each of the plurality of first wavelength bands for each of the second spatial regions;
   illuminating at least part of an object with the at least one third light beam to produce at least one fourth light beam, the at least one fourth light beam comprising a plurality of fourth spatial regions, each of the fourth spatial regions comprising a plurality of second wavelength bands, at least two of the fourth spatial regions being spectrally different;
   measuring a spectrum in each of the plurality of second wavelength bands for each of the fourth spatial regions; and
   identifying a radiance transfer factor of the object using at least some of the measured spectra.

2. The method of claim 1, further comprising identifying a color of the object under a specified illumination condition using the radiance transfer factor.

3. The method of claim 1, wherein:
   measuring the spectrum in each of the first wavelength bands comprises using a first detector; and
   measuring the spectrum in each of the second wavelength bands comprises using a second detector.

4. The method of claim 3, further comprising calibrating the first and second detectors.

5. The method of claim 4, wherein calibrating the first and second detectors comprises at least one of:
   using spectrally localized features in one or more spatial regions in each of the second and fourth light beams to calibrate wavelength scales of the detectors;
   using spectral features of one or more spatial regions in each of the second and fourth light beams to establish a correspondence between the second and fourth light beams at the detectors; and
   using a second object having a known reflectance or transmittance to calibrate photometric scales of the detectors.

6. The method of claim 1, wherein generating the at least one second light beam and the at least one third light beam comprises splitting the first light beam.

7. The method of claim 6, further comprising one or more of diffusing, collimating, focusing, and filtering light from one or more light sources to generate the first light beam.

8. The method of claim 1, wherein the first light beam comprises one or more of:
   a single light beam having one or more first spatial regions; and
   multiple light beams each having one or more first spatial regions.

9. The method of claim 1, further comprising interrupting the illuminating of at least part of the object;
   wherein measuring the spectrum in each of the plurality of second wavelength bands for each of the fourth spatial regions comprises measuring the spectrum in each of the plurality of second wavelength bands for each of the fourth spatial regions both before and after interrupting the illuminating; and
   wherein the radiance transfer factor comprises a phosphorescent radiance transfer factor.

10. The method of claim 1, wherein:
    the first wavelength bands are equal to the second wavelength bands; and
    each spatial region in the at least one second light beam and the at least one fourth light beam is substantially homogenous spectrally.

11. An apparatus, comprising:
    a beam generator configured to:
       generate a first light beam comprising a plurality of first spatial regions, at least two of the first spatial regions being spectrally different; and
       generate at least one second light beam and at least one third light beam using the first light beam, the at least one second light beam comprising a plurality of second spatial regions, each of the second spatial regions comprising a plurality of first wavelength bands, the at least one third light beam comprising a plurality of third spatial regions, at least two of the second spatial regions being spectrally different, at least two of the third spatial regions being spectrally different;

a first detector configured to measure a spectrum in each of the plurality of first wavelength bands for each of the second spatial regions; and a second detector configured to measure a spectrum in each of a plurality of second wavelength bands for each of a plurality of fourth spatial regions in at least one fourth light beam, at least two of the fourth spatial regions being spectrally different, the at least one fourth light beam generated by illuminating at least part of an object with the at least one third light beam.

12. The apparatus of claim 11, further comprising a controller configured to at least one of:

identify a radiance transfer factor of the object using at least some of the measured spectra; and identify a color of the object under a specified illumination condition using the radiance transfer factor.

13. The apparatus of claim 12, wherein:

the illuminating of at least part of the object is interrupted;

the second detector is configured to measure the spectrum in each of the second wavelength bands for each of the fourth spatial regions both before and after the illuminating is interrupted; and the radiance transfer factor comprises a phosphorescent radiance transfer factor.

14. The apparatus of claim 11, wherein each detector comprises an array of detector elements arranged in rows and columns, each row measuring the spectra of the wavelength bands associated with a single one of the spatial regions, each column measuring the spectra of wavelength bands associated with different ones of the spatial regions.

15. The apparatus of claim 11, wherein the beam generator comprises:

one or more light sources;

at least one of: one or more diffusers, one or more collimators, one or more lenses, and one or more filters configured to generate the first light beam; and one or more splitters configured to split the first light beam to produce the at least one second light beam and the at least one third light beam.

16. The apparatus of claim 11, wherein the beam generator comprises:

at least one calibration filter configured to impose spectral features on the first light beam, the spectral features used at least during calibration of the apparatus.

17. The apparatus of claim 16, further comprising a second object having a known reflectance or transmittance used at least during the calibration of the apparatus.

18. An apparatus, comprising:

beam generating means configured to:

generate a first light beam comprising a plurality of first spatial regions, at least two of the first spatial regions being spectrally different; and generate at least one second light beam and at least one third light beam using the first light beam, the at least one second light beam comprising a plurality of second spatial regions, each of the second spatial regions comprising a plurality of first wavelength bands, the at least one third light beam comprising a plurality of third spatial regions, at least two of the second spatial regions being spectrally different, at least two of the third spatial regions being spectrally different;

first measuring means configured to measure a spectrum in each of the plurality of first wavelength bands for each of the second spatial regions; and second measuring means configured to measure a spectrum in each of a plurality of second wavelength bands for each of a plurality of fourth spatial regions in at least one fourth light beam, at least two of the fourth spatial regions being spectrally different, the at least one fourth light beam generated by illuminating at least part of an object with the at least one third light beam.

19. The apparatus of claim 18, further comprising calculating means configured to at least one of:

identify a radiance transfer factor of the object using at least some of the measured spectra; and identify a color of the object under a specified illumination condition using the radiance transfer factor.

20. The apparatus of claim 18, wherein the beam generating means comprise:

light generating means configured to produce light;

at least one of: diffusing means, collimating means, focusing means, and filtering means configured to use the light from the light generating means to generate the first light beam; and splitting means configured to split the first light beam to produce the at least one second light beam and the at least one third light beam.

* * * * *